(12) United States Patent
Southard et al.

(10) Patent No.: US 11,020,563 B2
(45) Date of Patent: Jun. 1, 2021

(54) AUTOMATED CATHETER-TO-VESSEL SIZE COMPARISON TOOL AND RELATED METHODS

(71) Applicant: C. R. Bard, Inc., Murray Hill, NJ (US)

(72) Inventors: Jeanette E. Southard, Park City, UT (US); Matthew J. Prince, West Jordan, UT (US); Arthur E. Jaquez, Salt Lake City, UT (US); Carr A. Harvey, North Salt Lake, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 628 days.

(21) Appl. No.: 15/650,474

(22) Filed: Jul. 14, 2017

(65) Prior Publication Data

US 2018/0015256 A1  Jan. 18, 2018

Related U.S. Application Data

(60) Provisional application No. 62/362,458, filed on Jul. 14, 2016.

(51) Int. Cl.
*A61M 25/01* (2006.01)
*G06T 7/00* (2017.01)
(Continued)

(52) U.S. Cl.
CPC ..... *A61M 25/0105* (2013.01); *A61B 5/02007* (2013.01); *A61B 5/107* (2013.01);
(Continued)

(58) Field of Classification Search
CPC ...... A61M 25/0105; A61M 2025/0166; A61B 8/0841; A61B 5/1076; A61B 5/02007;
(Continued)

(56) References Cited

U.S. PATENT DOCUMENTS 5,148,809 A  9/1992  Biegeleisen-Knight et al.
5,181,513 A  1/1993  Touboul et al.
(Continued)

FOREIGN PATENT DOCUMENTS

EP  1591074 B1  5/2008
WO  2014/115150 A1  7/2014
(Continued)

*Primary Examiner* — Hien N Nguyen
(74) *Attorney, Agent, or Firm* — Rutan & Tucker LLP

(57) ABSTRACT

Systems and methods for assisting the placement of a catheter within a vessel of a patient via an ultrasound imaging system are disclosed. The systems and methods described herein relate to an automatic size comparison tool to enable a clinician to determine, prior to insertion of the catheter, whether a particularly sized catheter will fit within a designated vessel of the patient without violating a user-defined rule setting a maximum percentage of the vessel that may be occupied by the catheter. This in turn ensures that the catheter is properly sized for the vessel in which it is placed, according to user-defined preferences. Though described herein as implemented in connection with an ultrasound imaging system, in other embodiments the system and methods described herein can be included with other devices as well.

35 Claims, 6 Drawing Sheets

US 11,020,563 B2

Page 2

(51) Int. Cl.
*A61B 5/107* (2006.01)
*G06T 7/62* (2017.01)
*A61B 8/00* (2006.01)
*A61B 5/02* (2006.01)
*A61B 8/08* (2006.01)

(52) U.S. Cl.
CPC .......... *A61B 5/1076* (2013.01); *A61B 8/0841* (2013.01); *A61B 8/465* (2013.01); *G06T 7/0014* (2013.01); *G06T 7/62* (2017.01); *A61M 2025/0166* (2013.01); *G06T 2207/10132* (2013.01); *G06T 2207/30021* (2013.01); *G06T 2207/30101* (2013.01)

(58) Field of Classification Search
CPC .......... A61B 8/465; A61B 5/107; G06T 7/62; G06T 7/0014; G06T 2207/10132; G06T 2207/30021; G06T 2207/30101
See application file for complete search history.

(56) References Cited

U.S. PATENT DOCUMENTS

| | | | |
|---|---|---|---|
| 5,325,293 A | 6/1994 | Dorne |
| 5,441,052 A | 8/1995 | Miyajima |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,132,379 A | 10/2000 | Patacsil et al. |
| 6,233,476 B1 | 5/2001 | Strommer et al. |
| 6,245,018 B1 | 6/2001 | Lee |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,592,520 B1 | 7/2003 | Peszynski et al. |
| 6,592,565 B2 | 7/2003 | Twardowski |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,060,181 B2 | 11/2011 | Rodriguez Ponce et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,790,263 B2 | 7/2014 | Randall et al. |
| 8,939,908 B2 | 1/2015 | Suzuki et al. |
| 8,961,420 B2 | 2/2015 | Zhang |
| 9,022,940 B2 | 5/2015 | Meier |
| 9,138,290 B2 | 9/2015 | Hadjicostis |
| 9,204,858 B2 | 12/2015 | Pelissier et al. |
| 9,220,477 B2 | 12/2015 | Urabe et al. |
| 9,295,447 B2 | 3/2016 | Shah |
| 9,320,493 B2 | 4/2016 | Visveshwara |
| 9,357,980 B2 | 6/2016 | Toji |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,804 B2 | 10/2016 | Tamada |
| 9,468,413 B2 | 10/2016 | Hall et al. |
| 9,582,876 B2 | 2/2017 | Specht |
| 9,610,061 B2 | 4/2017 | Ebbini et al. |
| 9,649,037 B2 | 5/2017 | Lowe et al. |
| 9,702,969 B2 | 7/2017 | Hope Simpson et al. |
| 9,715,757 B2 | 7/2017 | Ng et al. |
| 9,717,415 B2 | 8/2017 | Cohen |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,043,272 B2 | 8/2018 | Forzoni et al. |
| 2003/0047126 A1 | 3/2003 | Tomaschko |
| 2005/0049504 A1 | 3/2005 | Lo et al. |
| 2005/0267365 A1 | 12/2005 | Sokulin et al. |
| 2006/0015039 A1 | 1/2006 | Cassidy et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0199848 A1 | 8/2007 | Ellswood et al. |
| 2008/0021322 A1 | 1/2008 | Stone et al. |
| 2008/0033293 A1* | 2/2008 | Beasley .................. A61B 8/00 600/437 |
| 2008/0033759 A1 | 2/2008 | Finlay |
| 2008/0146915 A1 | 6/2008 | McMorrow |
| 2008/0221425 A1 | 9/2008 | Olson et al. |
| 2008/0294037 A1 | 11/2008 | Richter |
| 2009/0012399 A1 | 1/2009 | Sunagawa et al. |
| 2009/0143672 A1 | 6/2009 | Harms et al. |
| 2011/0002518 A1 | 1/2011 | Liv-Ari et al. |
| 2012/0197132 A1 | 8/2012 | O'Connor |
| 2012/0220865 A1 | 8/2012 | Brown et al. |
| 2012/0277576 A1 | 11/2012 | Lui |
| 2013/0041250 A1 | 2/2013 | Pelissier et al. |
| 2013/0102889 A1* | 4/2013 | Southard .............. A61B 8/0841 600/424 |
| 2013/0131502 A1 | 5/2013 | Blaivas et al. |
| 2013/0150724 A1 | 6/2013 | Blaivas et al. |
| 2014/0005530 A1 | 1/2014 | Liu et al. |
| 2014/0073976 A1 | 3/2014 | Fonte et al. |
| 2014/0100440 A1 | 4/2014 | Cheline et al. |
| 2014/0180098 A1 | 6/2014 | Flaherty et al. |

(56) References Cited

U.S. PATENT DOCUMENTS

| | | |
|---|---|---|
| 2014/0188133 A1* | 7/2014 | Misener ............ A61M 25/0102 |
| | | 606/130 |
| 2014/0188440 A1 | 7/2014 | Donhowe et al. |
| 2014/0276059 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai |
| 2015/0209113 A1 | 7/2015 | Burkholz et al. |
| 2015/0209526 A1 | 7/2015 | Matsubara et al. |
| 2015/0297097 A1 | 10/2015 | Matsubara et al. |
| 2016/0113699 A1* | 4/2016 | Sverdlik .................. A61N 7/00 |
| | | 606/27 |
| 2016/0120607 A1 | 5/2016 | Sorotzkin et al. |
| 2016/0166232 A1 | 6/2016 | Merritt |
| 2016/0202053 A1 | 7/2016 | Walker et al. |
| 2016/0278869 A1 | 9/2016 | Grunwald |
| 2016/0296208 A1 | 10/2016 | Sethuraman et al. |
| 2016/0374644 A1 | 12/2016 | Mauldin, Jr. et al. |
| 2017/0367678 A1 | 12/2017 | Sirtori et al. |
| 2018/0116723 A1 | 5/2018 | Hettrick et al. |
| 2018/0125450 A1 | 5/2018 | Blackboume et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |

FOREIGN PATENT DOCUMENTS

| | | |
|---|---|---|
| WO | 2017096487 A1 | 6/2017 |
| WO | 2017214428 A1 | 12/2017 |
| WO | 2018134726 A1 | 7/2018 |

* cited by examiner

AUTOMATED CATHETER-TO-VESSEL SIZE COMPARISON TOOL AND RELATED METHODS

CROSS-REFERENCE TO RELATED APPLICATIONS

This application claims the benefit of U.S. Provisional Patent Application No. 62/362,458, filed Jul. 14, 2016, and entitled "Automated Catheter-to-Vessel Size Comparison Tool and Related Methods," which is incorporated herein by reference in its entirety.

BRIEF SUMMARY

Briefly summarized, embodiments of the present invention are directed to systems and methods for assisting the placement of a catheter within a vessel of a patient via an ultrasound imaging system. The systems and methods described herein relate to an automatic size comparison tool to enable a clinician to determine, prior to insertion of the catheter, whether a particularly sized catheter will fit within a designated vessel of the patient without violating a user-defined rule setting a maximum percentage of the vessel that may be occupied by the catheter. This in turn ensures that the catheter is properly sized for the vessel in which it is placed, according to user-defined preferences, and does not unduly impede blood flow through the vessel.

In one embodiment, therefore, an ultrasound imaging system comprises a probe, a display configured to depict an ultrasound image of a subcutaneous patient vessel of the patient produced by the probe, and an automatic vessel size comparison tool. The vessel size comparison tool is configured to be used in preparation for inserting a catheter into the vessel of the patient and comprises a rule user interface configured to enable a user of the system to define a vessel occupancy rule defining a maximum amount of occupation of a sample vessel by a sample catheter. The comparison tool is configured to automatically depict occupation information on the display. The occupancy information relates to the vessel occupancy rule and is depicted when an image of the patient vessel is produced by the imaging system and when a size of the sample catheter has been selected. In one embodiment, the occupancy information includes a comparison between the selected sample catheter size and a minimum size of a sample vessel that satisfies the vessel occupancy rule.

Though described herein as implemented in connection with an ultrasound imaging system, in other embodiments the system and methods described herein can be included with other devices as well.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to systems and methods for assisting the placement of an elongate medical device, such as a catheter, within a vessel or other suitable location within the body of a patient through the use of an ultrasound imaging system. In particular, the systems and methods described herein relate to an automatic size comparison tool enable a clinician to determine, prior to insertion of the medical device, whether a particularly sized catheter will fit within a designated vessel of the patient without violating a user-defined rule setting a maximum percentage of the vessel that may be occupied by the catheter. This in turn ensures that the catheter is properly sized for the vessel in which it is placed, according to user-defined preferences. Though described herein as implemented in connection with an ultrasound imaging system, in other embodiments the system and methods described herein can be included with other devices as well.

Figure 1:
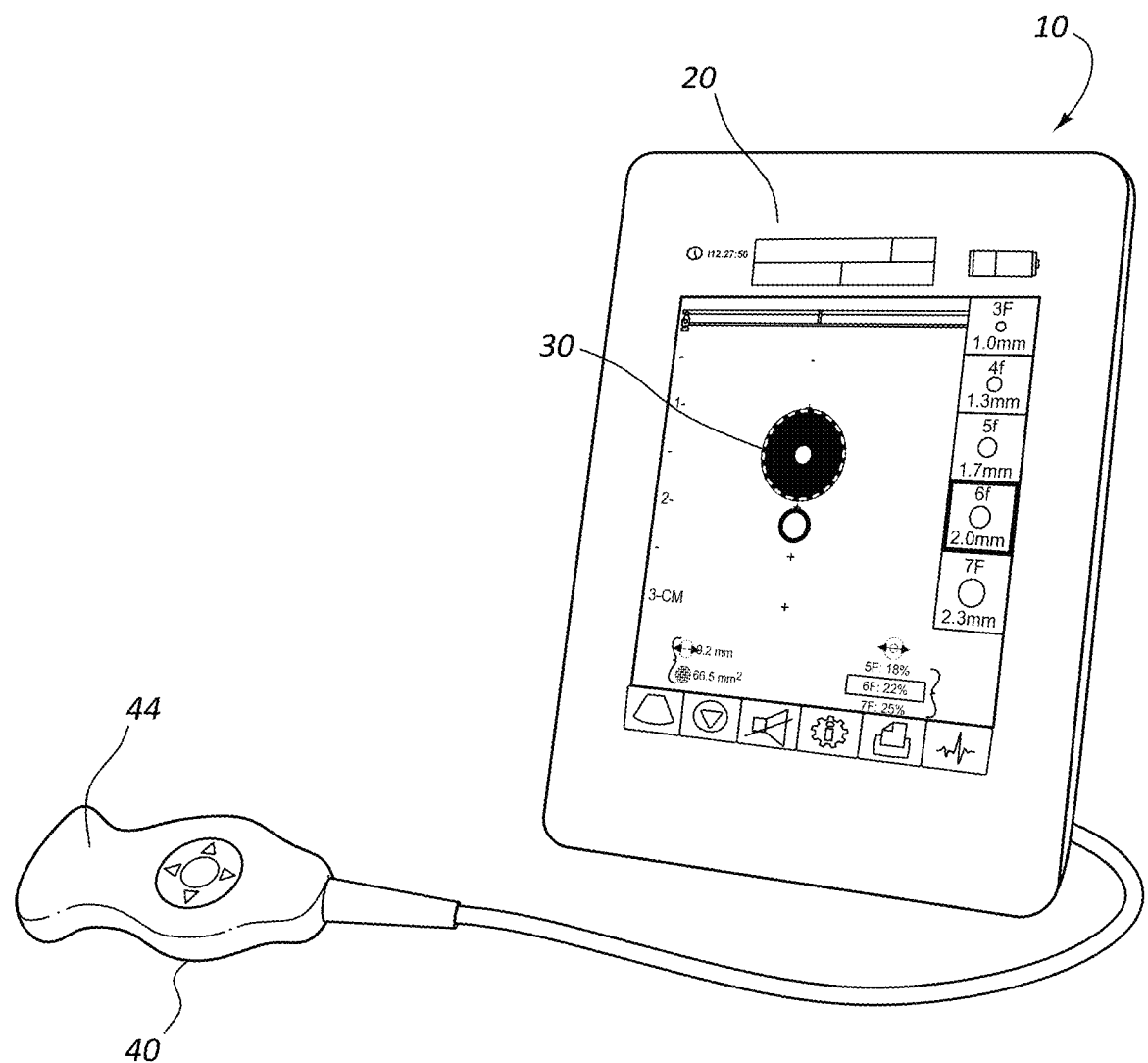
FIG. 1 is a perspective view of an ultrasound imaging system according to one embodiment.

FIG. 1 shows various components of an ultrasound imaging system 10 (also referred to herein as "imaging system" or "system"), according to one embodiment. As shown, the system 10 includes a console 20 housing various electronic and other components necessary for processing and depicting ultrasonic images. The console 20 includes a touchscreen display 30 for depicting ultrasonic images and for enabling touch-based input by a clinician to control the device and its functionality. A probe 40, containing one or more transducer elements in a head 44 thereof for emitting and receiving ultrasonic signals, is operably attached to the console 20 via a cable or other suitable interface.

In one embodiment, an optional cap including a hydrogel insert can be removably attached to the head 44 of the probe 40 so as to cover the transducer elements disposed therein. The hydrogel insert provides an ultrasonically transparent interface between the probe head 44 and the skin surface. A needle guide can also be included with the cap to assist with guiding needles through the patient's skin and into the vessel being imaged by the system 10. In another embodiment, the needle guide is included on the probe itself. Further details regarding the probe cap, hydrogel insert, and needle guide can be found in U.S. patent application Ser. No. 13/206,396, filed Aug. 9, 2011, and entitled "Support and Cover Structures for an Ultrasound Probe Head," and U.S. patent application Ser. No. 13/531,406, filed Jun. 22, 2012, and entitled "Needle Guide with Selectable Aspects." Each of the foregoing applications is incorporated herein by reference in its entirety. Note that other ultrasound imaging devices and systems that differ from that shown here can also benefit from the embodiments described herein.

Figure 2:
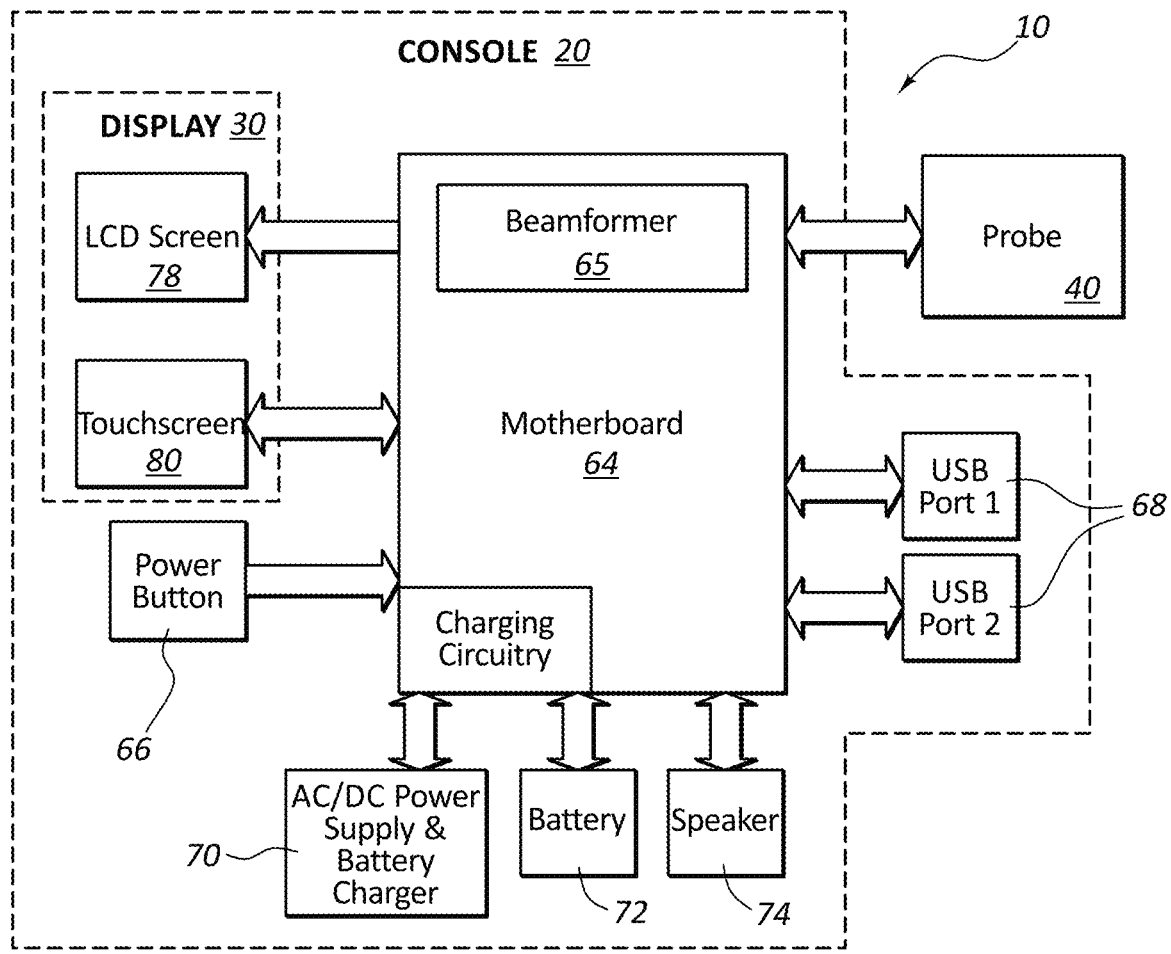
FIG. 2 is a block diagram showing various components of the ultrasound imaging system of FIG. 1.

FIG. 2 shows a block diagram of the system 10 of FIG. 1, according to one embodiment. In detail, the console 20, display 30, and probe 40 are represented, as in FIG. 1. The console 20 includes therein a motherboard 64 for governing system functionality and includes a processor or other general or special purpose computer, memory, storage locations, and other components for system operation. A beamformer 65, including suitable circuitry, is also operably included with the motherboard 64 to enable ultrasonic signals to be produced, received, and processed. A power button 66 is included, as are USB ports 68 for interfacing with other devices. An external power supply 70, as well as a battery 72 and speaker 74, are provided for operation. The display 30 in the present embodiment includes an LCD screen 78 or other suitable screen, and a touchscreen 80 to enable touch-based functionality via the display 30. Note that the system 10 can include different, fewer, or more components than those listed here, including those components that enable the system to operate in a networked manner with other local or remote computing or network systems, including for instance, Wi-Fi, Ethernet, Bluetooth, and ZigBee functionality. Also, in addition to a touchscreen, other input modes can also be employed, including a keyboard or mouse input, for instance.

In operation of the system 10, the probe 40 is placed against the skin of the patient so as to ultrasonically image a cross-sectional slice of a vessel, such as a vein, or other internal body tissue of the patient below the surface of the skin. Indeed, a target location of the vessel imaged by the probe 40 is disposed a substantially vertical depth below the end of the probe. The vessel is imaged by the system 10 in preparation for accessing the vessel with a needle in preparation for inserting a catheter into the vessel, in one embodiment. Though shown here as a vessel, the target location can be any one of various subcutaneous locations within the body.

Figure 3:
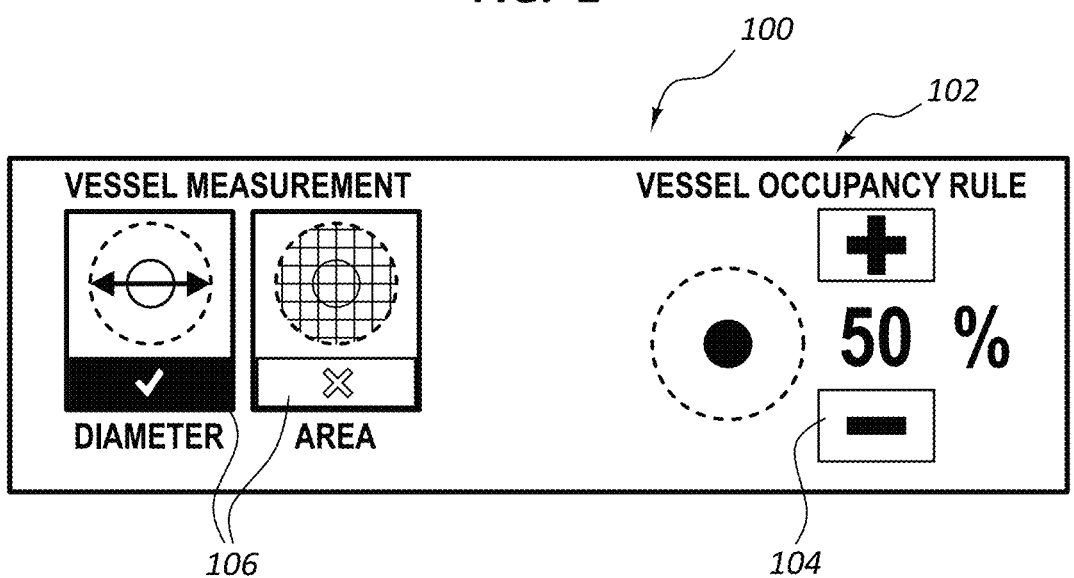
FIG. 3 shows a depiction of the display of the ultrasound imaging system of FIG. 1.

FIG. 3 depicts various details regarding one portion of an automatic vessel size comparison tool for assisting a user of the system 10 in choosing a properly sized catheter for insertion into an ultrasonically imaged vessel of the patient, according to one embodiment. In detail, FIG. 3 shows a rule user interface depiction (also "user interface depiction") 100 that is depicted on the display 30 prior to/during the above-described ultrasonic imaging operation by the imaging system 10, according to one embodiment. The user interface depiction 100 can be included as part of a settings menu depicted on the display 30 to enable a user of the system 10 to customize one or more settings of the system.

As shown in FIG. 3, the user interface depiction 100 includes settings 102 that enable a clinician or other user to define a vessel occupancy rule, which dimensionally specifies how much of a sample vessel (representing a cross-sectional, ultrasonically imaged patient vessel) can be occupied by a sample catheter if it were inserted therein. When this vessel occupancy rule is implemented by the automatic size comparison tool as described below, the clinician using the system 10 is able to determine which size of catheter is suitable for insertion into the imaged patient vessel without violating the vessel occupancy rule.

As shown, the settings 102 include a rule selector 104 for selecting the percentage amount of a sample vessel (represented in cross section) that can be occupied by a selected sample catheter (discussed further below). The percentage amount (here showing a vessel occupancy rule of 50%) can be toggled up or down by the corresponding + or − buttons, respectively. In one embodiment, the icon to the left of the rule selector 104, including a dashed-line circle representing the cross-sectional sample vessel and a solid inner circle representing the size of the sample catheter, can vary in size relative to each other (according to the selected percentage amount) in order to graphically depict the level of vessel occupancy by the catheter. Though the range of vessel occupancy that can be set via the rule selector 104 can vary, in one embodiment the range extends from about 5 percent to about 100%. In one embodiment, the vessel occupancy rule is pre-set by the system 10 until altered by a user via the rule selector 104.

The settings 102 further include a vessel measurement selector 106 to enable the user to designate whether the vessel occupancy rule is dimensionally based on vessel diameter or vessel cross-sectional area. As such, FIG. 3 shows for instance that the user has specified that a catheter should occupy no more than 50% of the vessel (via the rule selector 104) as measured by vessel diameter (via the vessel measurement selector 106). In addition to these settings, additional vessel occupancy settings can be depicted on the display 30, in other embodiments.

In the present embodiment, it is noted that vessel occupancy is determined by the system in the following ways: for vessel diameter: % occupied=[diameter of sample catheter/diameter of vessel comparison ring (described below)]×100; for vessel area: % occupied=[area of sample catheter/area of vessel comparison ring]×100.

Figure 4:
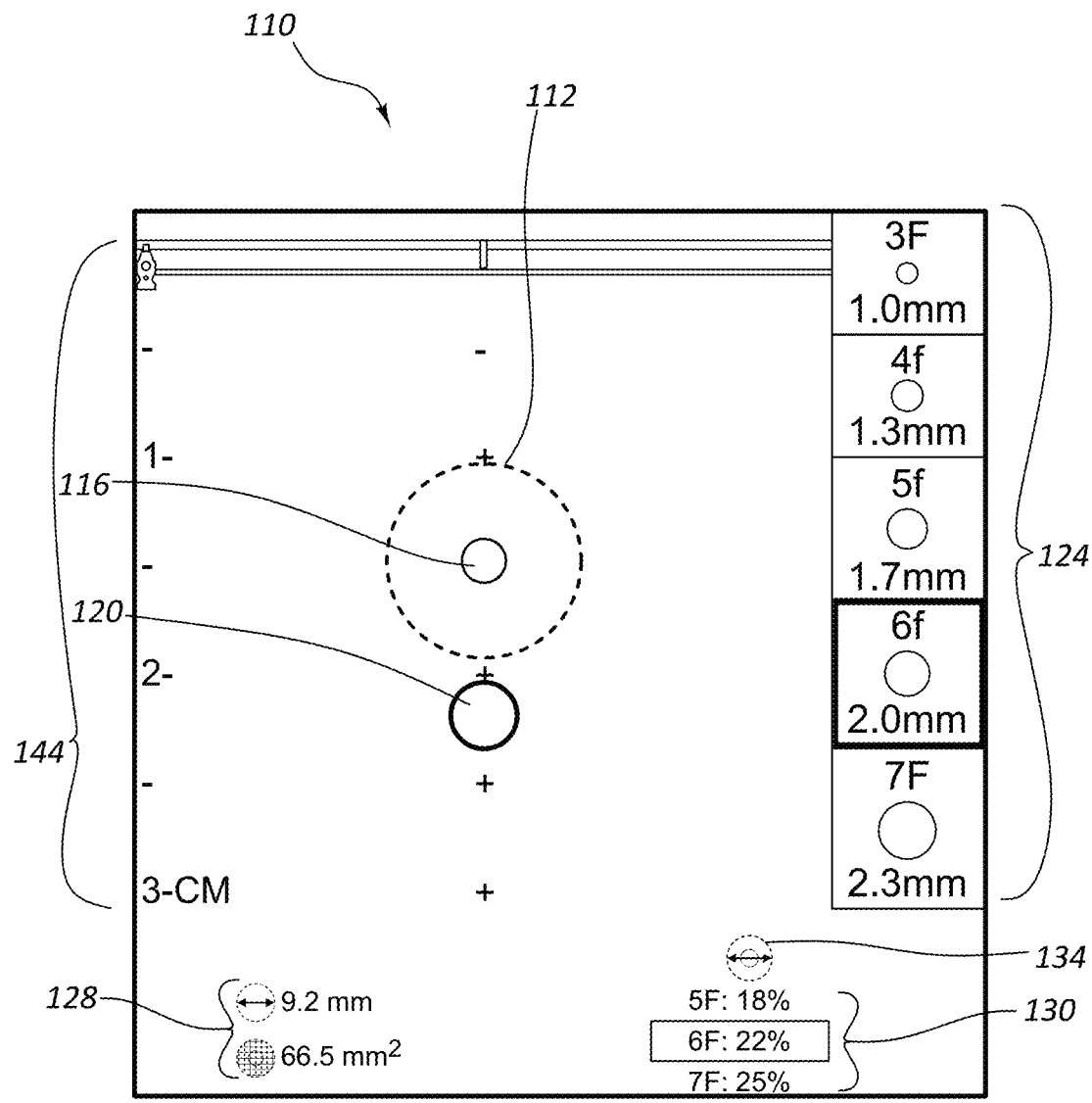
FIG. 4 depicts various elements of a comparison tool according to one embodiment.

FIG. 4 shows various details of a user interface 110 of the automatic vessel size comparison tool according to one embodiment. As shown, the user interface 110 is configured for depiction on the system display 30 during the above-described ultrasonic imaging operation of the vessel of the patient by the imaging system 10. Indeed, the elements to be described are configured to be superimposed over an ultrasonic cross-sectional image of the patient vessel on the display 30 during a catheter placement or other suitable procedure in order to assist the clinician in deciding an appropriately sized catheter to be inserted into the patient, as will be seen further below.

The user interface 110 includes a vessel comparison ring 112 including a dashed-line circle that represents a sample vessel in cross section, wherein the dashed circle outlines the perimeter boundary of the sample vessel. Thus, the vessel comparison ring virtually represents a cross-sectional slice of the patient vessel, such as that imaged by the system 10 and depicted on the display 30 (see, e.g., vessel 142 in FIG. 5).

In one embodiment, the vessel comparison ring 112 is depicted on the display 30 with a predetermined size 112 and can be manipulated in size by the user in order to match the size of the perimeter of the patient vessel in the ultrasound image, as discussed further below. In another embodiment, the initial size of the vessel comparison ring 112 is automatically determined by the system 10 following automatic detection of the vessel on the ultrasound image. Indeed, in one embodiment, a processor or other suitable component of the motherboard 64 of the system 10 (FIG. 2) can execute one or more algorithms to automatically detect the presence of a vessel in the ultrasound image of the vessel captured by the system 10 during operation. These algorithms take advantage of the fact that blood vessels represent a rapid gradient change compared to surrounding tissue when viewed ultrasonically, due to the relative density difference between the two. Further, vessels are typically round and possess a relatively ultrasonically homogenous interior structure, which further assist algorithms in detecting vessels in an ultrasonic image.

In greater detail, in one embodiment vessel detection is an automated process performed by algorithm. First, a data set represented by the ultrasonic image is presented for analysis. Vessel and tissue boundaries are detected via application of an edge detection filter, such as a Canny or Sobel filter. Convolution is then applied to the resultant data set of identified candidate vessels to map approximated centers of the vessels. Multiple circle kernels may be applied during convolution corresponding to known or likely vessel diameters. These techniques result in the vessel being automatically identified and sized within the ultrasound image, thus enabling matching of the size of the vessel comparison ring 112 to the vessel perimeter. In addition to these, other vessel detection techniques are contemplated.

The user interface 110 of FIG. 4 further includes a catheter size icon 116 that is centered in the vessel comparison ring 112 and is sized according to the size of a sample catheter selected by the clinician on a catheter size selection menu 124, here located on the right side of the user interface. The sizes of the catheter size icon 116 and the catheters represented in the catheter size selection view 124 are proportional to the scale of the ultrasound image. For instance, the size scale of the ultrasound image that would be depicted in FIG. 4 is in centimeters (cm), as can be determined by reference to depth markings 144 shown on the left side of the user interface 110. Other dimensional units could be used. In the present embodiment the catheter size selection menu 124 can be toggled through by the clinician/user of the system 10 to depict differing size ranges of catheters according to use: peripheral IV, PICC (depicted in FIG. 4), CVC, dialysis. Of course, other catheter size groupings can be used.

A ring size control selector 120 is included below the vessel comparison ring 112 (though it can be positioned in other locations as well), and is employed to enable manual resizing of the vessel comparison ring by the user. As the display 30 is touchscreen and is therefore responsive to user touch, a clinician or other user can touch the display 30 at the size control icon 120 and move it vertically up or down to decrease or increase the size of the vessel comparison ring 112, respectively, to match the size of the perimeter of the ultrasonically imaged vessel, if needed. Also note that the vessel comparison ring 112 itself can be moved to align it with the ultrasonically imaged vessel in the same manner, that is, by touching the touchscreen-enabled display 30 at the approximate center of the vessel comparison ring 112 and moving it about as desired.

The user interface 110 further includes additional elements, such as vessel size data 128, which depicts the dimensions of the vessel comparison ring 112 in both diameter and cross-sectional area. The units shown in the present example are in millimeters (mm), though other units can be used. When the vessel comparison ring 112 is matched in size to the perimeter of the imaged vessel, the vessel size data 128 depicts as well the cross-sectional dimensions of the vessel.

Vessel occupation data 130 is also shown in the user interface 110, which depicts the percentage of vessel occupancy caused by the sample catheter size currently selected in the catheter size selection view 124. For instance, in the example shown in FIG. 4, a 6 French (Fr) catheter is selected in the catheter size selection view 124. The catheter size icon 116 depicts this catheter size as a solid circle in its centered position within the vessel comparison ring 112. The vessel occupation data 130 thus shows in the present example that the 6 French catheter would occupy approximately 22% of the vessel comparison ring 112, which corresponds in approximate size to the imaged vessel it superimposes. The percentage of vessel occupancy is also depicted by the vessel occupation data 130 for the next smaller and next larger French-size catheters, in this example, a 5 French (18%) and a 7 French (25%) catheter. A vessel measurement indicator 134 is also shown on the depiction 110, indicating whether the vessel occupancy percentage is based on vessel diameter or cross-sectional area, as selected by the user via the settings 102 of the depiction 100 (FIG. 3). In the present example shown in FIG. 4, the vessel measurement indicator 134 shows that the vessel occupancy percentage is based on vessel diameter. In addition, to vessel diameter and cross-sectional area, other dimensional relationships for the vessel could be employed.

Figure 5:
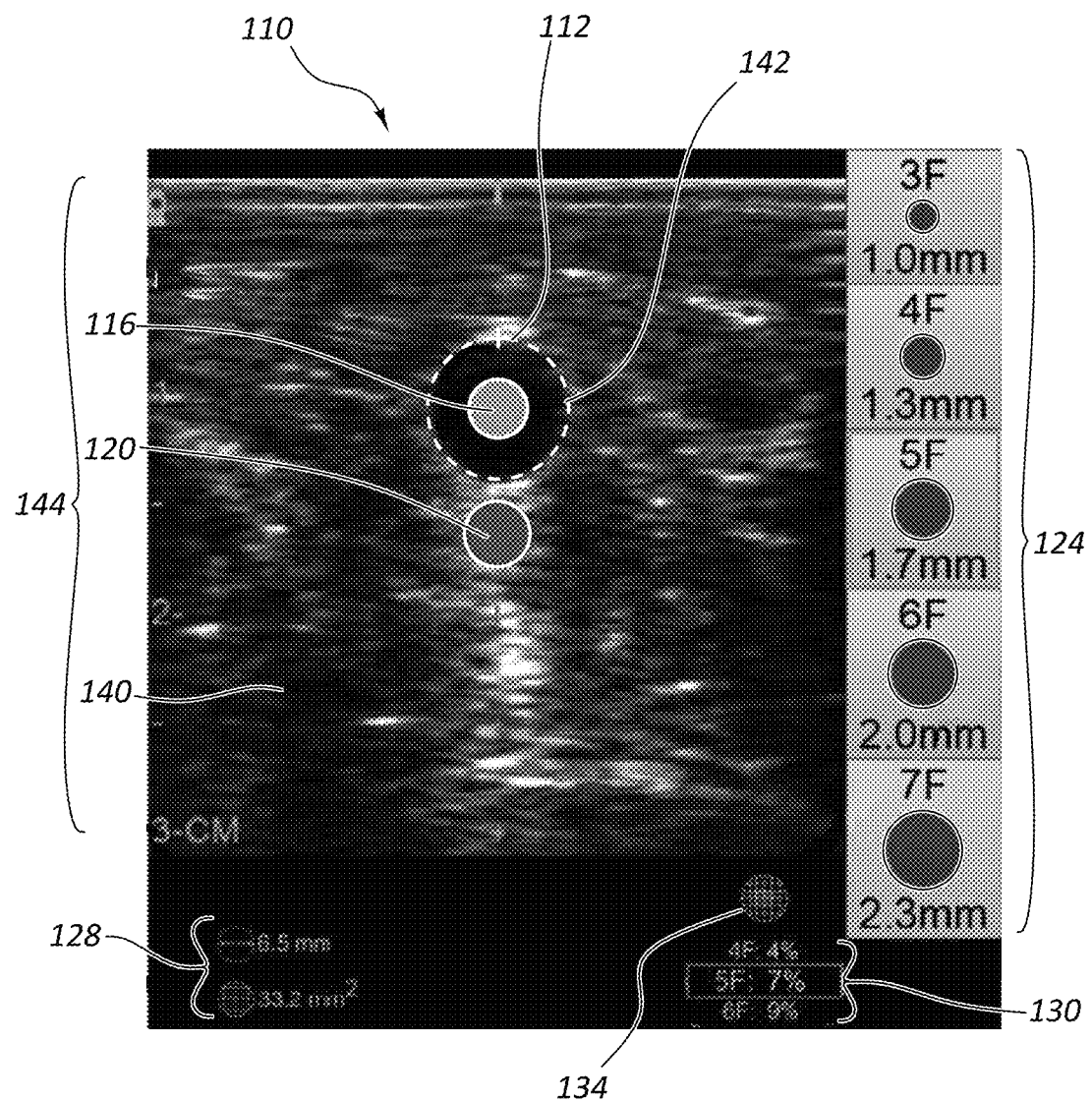
FIG. 5 depicts the elements of the comparison tool shown in FIG. 4 with an ultrasound image of the ultrasound imaging system of FIG. 1.

FIG. 5 depicts the various elements discussed above in connection with FIG. 4 included with an ultrasonic image 140 including an ultrasonically imaged patient vessel (also "vessel") 142, as an example of a depiction on the display 30 of the system 10 during an ultrasonic imaging operation to image the vessel prior to insertion therein of a catheter. As shown, the vessel comparison ring 112 is depicted, placed atop the cross-sectionally imaged vessel 142 so as to be centered therewith such that its perimeter matches that of the vessel. The other aforementioned elements are also present in the depiction, including the catheter size icon 116, the ring size control icon 120, the catheter size selection menu 124, the vessel size data 128, the vessel occupation data 130, and the vessel measurement indicator 134.

In greater detail and according to one embodiment, prior to or at the beginning of a catheter insertion procedure using the imaging system 10 (though other times are possible), the clinician navigates via the display 30 to the ultrasound settings screen including the settings 102 of the user interface depiction 100 as shown in FIG. 3 and selects the desired vessel occupancy rule by toggling the "+" and "−" buttons of the rule selector 104, as well as selecting either "diameter" or "area" as the type of vessel measurement to be used via the vessel measurement selector 106. Note that the vessel occupancy rule can be set at the beginning of each catheter insertion procedure using the system 10, or set only occasionally, wherein the system retains in its memory the previously set vessel occupancy rule.

Figure 6:
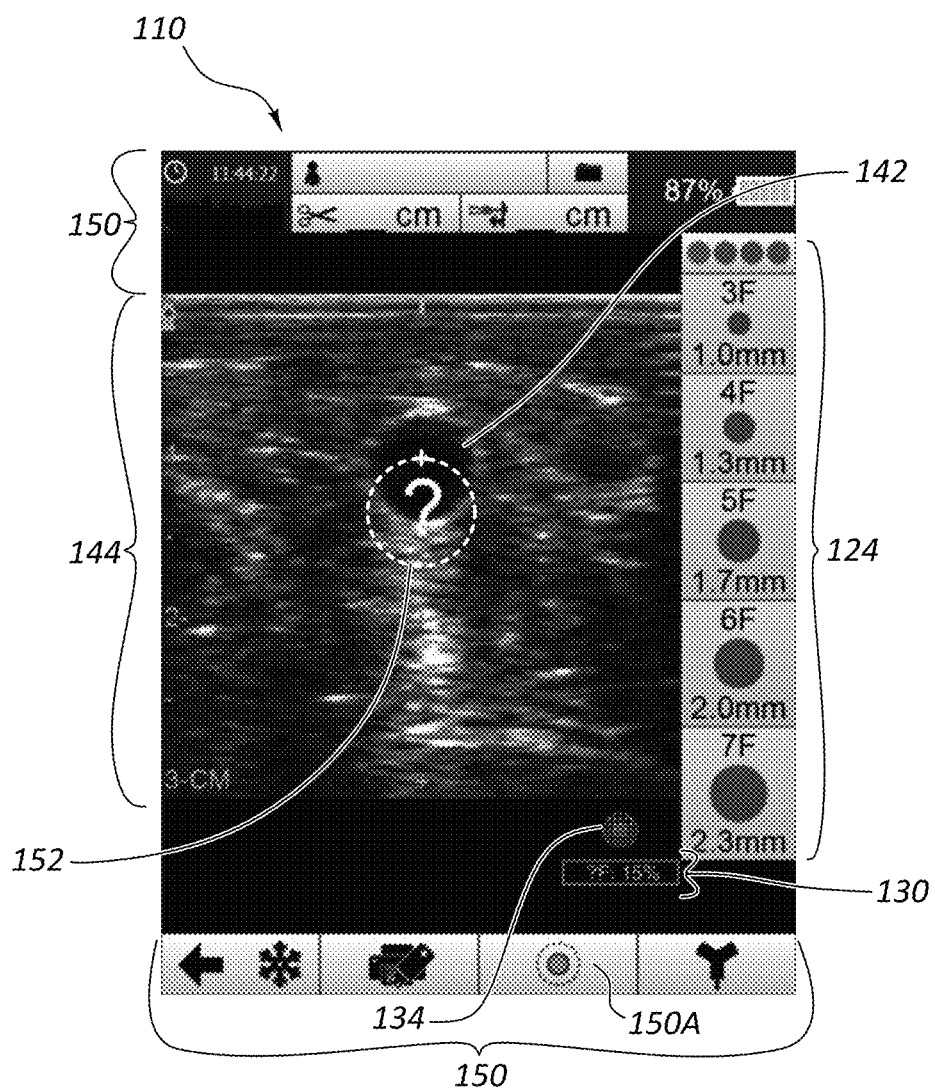
FIG. 6 is a depiction of a display of an ultrasound imaging system according to one embodiment.

Once the vessel occupancy rule is selected via the user interface depiction 100, the probe 40 of the system 10 is employed to ultrasonically image an internal portion of the patient body, such as internal portions of the arm, in order to image a vessel. The user then freezes the ultrasound image (using a touchscreen control button on the lower portion of operation icons 150 of the display 30 (or other suitable location/method)) to produce an image similar to the ultrasound image 140 of FIG. 6 and including a frozen image of the vessel 142. At this point the display 30 depicts an input awaiting icon 152 including a question mark, as shown in FIG. 6.

The user then opens the vessel measurement tool of the system 10 by pressing a control button 150A on a bottom portion of the touchscreen display 30 or other suitable location, which causes the various elements shown in FIG. 4 to be depicted on the display 30 together with the frozen ultrasound image, resulting in a depiction similar to that shown in FIG. 5. (It is appreciated in one embodiment that the automatic vessel size comparison tool described herein can be activated by the system without the need for pressing the button 150A, including automatic commencement when an ultrasound image is first depicted on the display.) The vessel comparison ring 112 in one embodiment is centered on the cross-sectionally imaged vessel 142 when the system includes automatic vessel detection as described further above, as in the present embodiment. In another embodiment where no automatic vessel detection is employed by the system 10, the vessel comparison ring 112 appears at a predetermined location on the display 30 and the clinician moves the vessel comparison ring 112 by pressing and holding in the center of the vessel comparison ring and sliding it on the display 30 until it is centered on the center of the imaged vessel 142.

No catheter size icon 116 is initially shown within the vessel comparison ring 112 until a particular sample catheter size is selected from the catheter size selection menu 124 via user touch to the touchscreen display 30. Once the catheter size has been selected, the catheter size icon 116 will appear within the vessel comparison ring 112. In the illustrated embodiment of FIG. 5, a 5 Fr catheter has been selected by the clinician, as indicated by the "5F" button of the catheter selection menu 124 being highlighted on the display 30. As such, the catheter size icon 116 is centered within the vessel comparison ring 112 and will be sized as a 5 Fr catheter according to the size scale of the ultrasound image 140. In another embodiment, a default sample catheter size can be selected by the system 10 when the automatic vessel comparison tool is activated on the system (by pressing the control button 150A (FIG. 6)). Such a default sample catheter size can be specified in the settings menu of the system 10, in one embodiment. In another embodiment, a default sample catheter size can be selected according to input into the system 10, such as by a bar code scanner, user manual entry, RFID reader technology, magnetic detection, etc.

Also at this point, the vessel comparison ring 112 is sized, with respect to the size of the catheter size icon 116 based on the selected sample catheter size (here 5 Fr), so as to satisfy the vessel occupancy rule selected by the user. That is, the size of the vessel comparison ring 112 will change in size to graphically represent the required cross-sectional size of a vessel that will not violate the maximum percentage amount of vessel occupancy when a catheter of the size of that selected in catheter selection menu 124 is present in the vessel. In the embodiment shown in FIG. 5, for instance, the vessel comparison ring 112 is sized to comply with a 7% vessel occupation rule (as indicated in the central position of the vessel occupation data 130) based on an area-based vessel measurement (as indicated by the vessel measurement indicator 134), with respect to a 5 Fr-sized catheter (as indicated by the size of the catheter size icon 116). Note that the selected vessel occupancy rule will be depicted in the central position of the vessel occupation data 130, along with the vessel occupancy percentage of the next larger and smaller catheter sizes (below and above, respectively). In addition, the vessel size data 128 and the vessel measurement indicator 134 will depict their respective information.

Figure 7A:
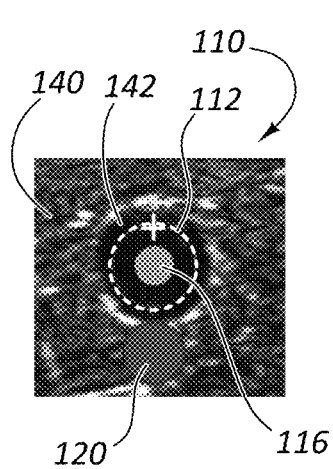
FIGS. 7A-7C show various views of portions of a display of an ultrasound imaging system according to one embodiment.
Figure 7B:
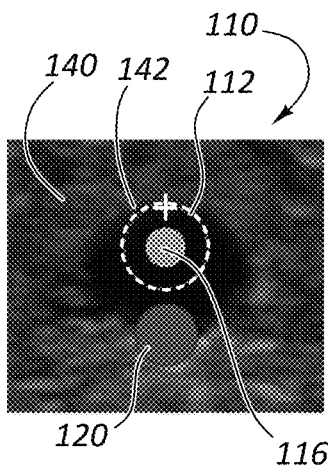
Figure 7C:
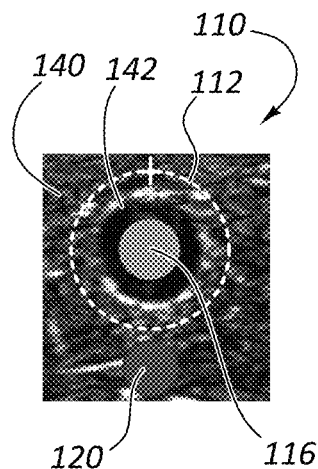

FIG. 7A shows the positional relationship of the vessel comparison ring 112, the catheter size icon 116, and the ring size control selector 120. FIG. 7B shows the case in which the cross-sectionally imaged vessel 142 is large enough to satisfy the vessel occupancy rule as indicated by the size of the relatively smaller vessel comparison ring 112. This indicates to the clinician that the selected catheter size, as indicated by the size of the catheter size icon 116, can be inserted into the imaged vessel without violating the vessel occupancy rule. In contrast, FIG. 7C shows the case in which the cross-sectionally imaged vessel 142 is not large enough to satisfy the vessel occupancy rule as indicated by the size of the relatively larger vessel comparison ring 112. This indicates to the clinician that the selected catheter size, as indicated by the size of the catheter size icon 116, cannot be inserted into the imaged vessel without violating the vessel occupancy rule.

Note that depiction of the vessel comparison ring 112 occurs automatically once an ultrasound image has been frozen on the display 30 and a catheter size has been selected from the catheter selection menu 124 (unless the catheter size is pre-selected or previously saved in system memory). Thus, no further action is required by the clinician to ascertain whether the catheter size selected suitable for insertion into the imaged vessel 142 without violating the previously set vessel occupancy rule. In another embodiment, some repositioning of the vessel comparison ring 112 may be necessary in order to center it over the imaged vessel 142. In yet another embodiment, other/additional conditions can be used to activate depiction of the vessel comparison ring 112.

Figure 8A:
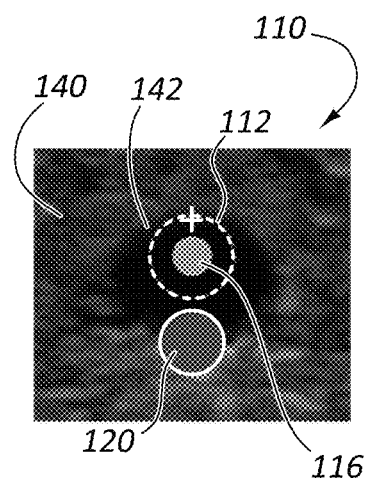
FIGS. 8A and 8B are various views of portions of a display of an ultrasound imaging system according to one embodiment.
Figure 8B:
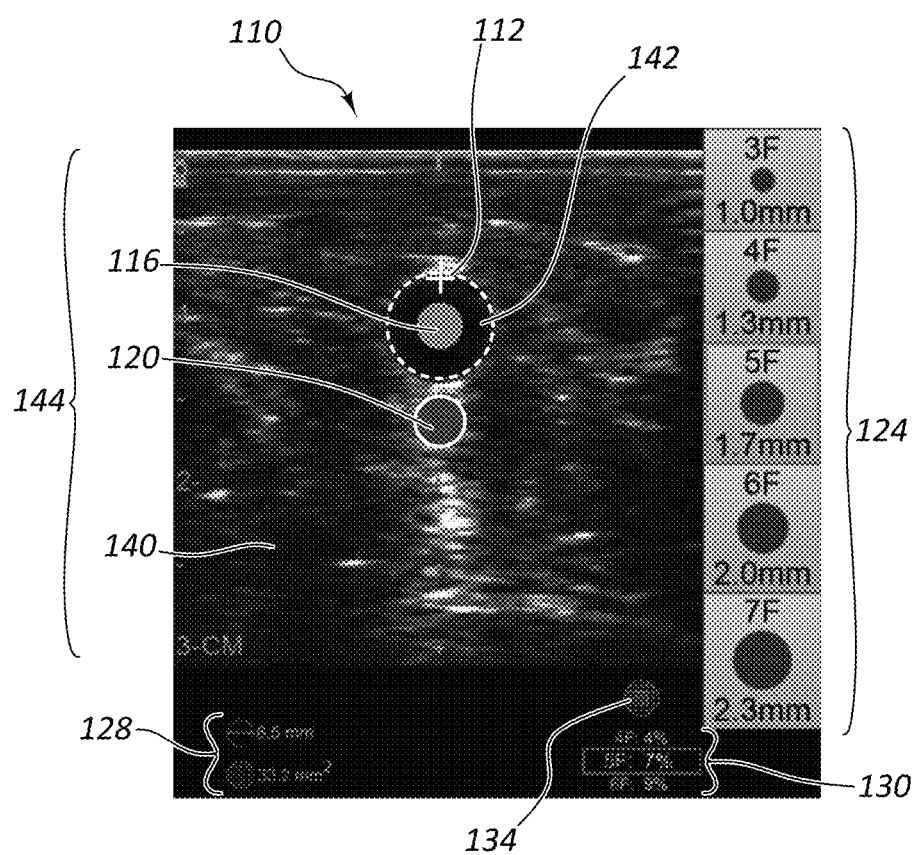

In the present embodiment and as mentioned above, the vessel comparison ring 112 is initially sized on the ultrasound image so as to correspond with the user-defined vessel occupancy rule once the desired catheter size is selected by the user from the catheter size selection menu 124. At this point, the vessel occupation data 130 will indicate in the central position thereof the selected vessel occupancy rule (which was initially selected in the settings 102 of the user interface depiction 100 in FIG. 3). Should the user wish to alter the size of the vessel comparison ring 112, such as to fit it to the size of the vessel 140 (in the case where automatic vessel detection is not employed by the system 10, for instance), the clinician touches and slides the ring size control selector 120 to match size of the vessel comparison ring to the size of the imaged vessel 142. This is illustrated in FIG. 8A, where the center of the vessel comparison ring 112 is touched on the touch screen display 30 and slid until a top portion of the vessel comparison ring (indicated by a "+" sign) is atop the top perimeter of the imaged vessel 142. The ring size control selector 120 is then touched and slid up/down on the display 30 until the vessel comparison ring 112 matches the perimeter of the imaged vessel 142, as is seen in FIG. 8B.

As a result of the above resizing of the vessel comparison ring 112, the vessel occupancy percentages depicted in the vessel occupation data 130 will correspondingly change to reflect the new vessel occupation percentage based on the new size of the vessel comparison ring 112.

Similarly, if—after the vessel comparison ring 112 is initially depicted on the display 30 so as to reflect the selected vessel occupancy rule—a new catheter size is selected from the catheter size selection menu 124, the vessel comparison ring 112 will correspondingly change in size so as to depict the required size of a vessel in order to preserve the selected vessel occupation rule. As before, the size of the vessel comparison ring 112 can be manually changed by the user at this point, which will then change the vessel occupancy percentages reflected in the vessel occupation data 130.

In the present embodiment, when the automatic vessel size comparison tool is initially selected by the user and the vessel comparison ring 112 is depicted on the display 30, the vessel comparison ring is not centered over the vessel 142, but is depicted at a predetermined location, such as a center point of the display. The vessel comparison ring 112 can be moved atop the imaged vessel 142 by the user touching and dragging the vessel comparison ring via touch the touchscreen display 30, as has been described further above. In another embodiment, the location of the vessel 142 on the display 30 is automatically detected by the system 10 and the vessel comparison ring 112 is placed atop the detected vessel.

Once the desired catheter size has been decided upon by the user by the above-described process, the user can unfreeze the display 30 and continue to use the ultrasound imaging of the system 10 to place a needle and subsequently the catheter, as may be desired.

It is appreciated that, in one embodiment, the ultrasound image of the patient vessel need not be frozen before the automatic vessel size comparison tool is depicted on the display; indeed, the vessel comparison ring and catheter size icon can be positioned at a suitable location on the display while the ultrasound imaging process is ongoing, provided that a sample catheter size has been selected. For instance, these elements can be positioned in a corner of the display, in one embodiment. In another embodiment, no freezing of the ultrasound image is needed prior to the automatic vessel size comparison tool being activated. One example of this is the case where automatic vessel detection is employed by the system 10; in this instance, the system identifies the vessel in the ultrasound image and launches the automatic vessel size comparison tool without the need for freezing of the image by the user.

In another embodiment, it is appreciated that the principles herein described can be applied to imaging systems other than ultrasound, such as x-ray/fluoroscopy, for instance. In yet another embodiment, the system can be employed in connection with subcutaneous regions other than vessels, such as fluid pockets, for instance. These and other uses are therefore contemplated.

Embodiments described herein may comprise a special purpose or general-purpose computer including computer hardware, as discussed in greater detail below. Embodiments within the scope of the present disclosure also include computer-readable media for carrying or having computer-executable instructions or data structures stored thereon. Such computer-readable media can be any available media that can be accessed by a general purpose or special purpose computer. By way of example, and not limitation, computer-readable media can comprise physical (or recordable-type) computer-readable storage media, such as, RAM, ROM, EEPROM, CD-ROM or other optical disk storage, magnetic disk storage or other magnetic storage devices, non-volatile memory (including flash memory), or any other medium which can be used to store desired program code means in the form of computer-executable instructions or data structures and which can be accessed by a general purpose or special purpose computer.

A "network" is defined herein as one or more data links that enable the transport of electronic data between computer systems and/or modules. When information is transferred or provided over a network or another communications connection (either hardwired, wireless, or a combination of hardwired or wireless) to a computer, the computer properly views the connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method for using an ultrasound imaging device for inserting a catheter into a body of a patient, the method comprising:
    selecting a vessel occupancy rule defining a maximum amount of occupation of a sample vessel by a sample catheter, wherein a minimum size of the sample vessel that satisfies the vessel occupancy rule is depicted by a vessel comparison ring;
    ultrasonically imaging a cross-sectional portion of a subcutaneous patient vessel of the patient by the ultrasound imaging device;
    by a user interface, selecting a size of the sample catheter for insertion into the subcutaneous patient vessel; and
    viewing occupancy information automatically generated by the ultrasound imaging device, wherein the occupancy information:
        relates to the vessel occupancy rule and the selected sample catheter size, and
        includes a percentage amount of occupancy of the sample vessel by the selected sample catheter.

2. The method for using as defined in claim 1, wherein selecting the size of the sample catheter and viewing the occupancy information are performed using a display of the ultrasound imaging device.

3. The method for using as defined in claim 2, wherein the display includes a touchscreen display.

4. The method for using as defined in claim 3, wherein the occupancy information includes a comparison between the selected sample catheter size and the minimum size of the sample vessel that satisfies the vessel occupancy rule.

5. The method for using as defined in claim 4, wherein the vessel comparison ring is a dashed circle.

6. The method for using as defined in claim 5, wherein viewing the occupancy information includes viewing on the display a depiction of the cross-sectional portion of the imaged subcutaneous patient vessel, the depiction including the vessel comparison ring and a cross-sectional representation of the selected sample catheter disposed within the vessel comparison ring.

7. The method for using as defined in claim 1, further comprising moving the vessel comparison ring atop the imaged subcutaneous patient vessel manually via touching and sliding on a display.

8. The method for using as defined in claim 6, wherein viewing the occupancy information further includes employing an automatic vessel detection by the ultrasound imaging device to place the vessel comparison ring atop the imaged subcutaneous patient vessel.

9. The method for using as defined in claim 7, wherein viewing the occupancy information further includes altering a size of the vessel comparison ring via touching and sliding a ring size control selector on the display.

10. The method for using as defined in claim 9, further comprising selecting a new size of the sample catheter after viewing the occupancy information.

11. The method for using as defined in claim 1, wherein selecting the vessel occupancy rule further comprises selecting the vessel occupancy rule by one of at least a diameter and an area of the sample vessel.

12. The method for using as defined in claim 1, wherein ultrasonically imaging the subcutaneous patient vessel includes freezing the imaged subcutaneous patient vessel on a display, and wherein selecting the size of the sample catheter further includes providing a command to the ultrasound imaging device prior to selecting the size of the sample catheter.

13. An ultrasound imaging system, comprising:
a probe;
a display configured to depict an ultrasound image of a subcutaneous patient vessel of a patient produced by the probe; and
an automatic vessel size comparison tool configured to be used in preparation for inserting a catheter into the subcutaneous patient vessel, the comparison tool comprising:
a rule user interface configured to enable a user of the ultrasound imaging system to define a vessel occupancy rule defining a maximum amount of occupation of a sample vessel by a sample catheter, wherein:
the comparison tool is configured to automatically depict on the display occupancy information relating to the vessel occupancy rule when an image of the subcutaneous patient vessel is produced by the ultrasound imaging system and when a size of the sample catheter has been selected,
the occupancy information includes a percentage amount of occupancy of the sample vessel by the selected sample catheter, and
a minimum size of the sample vessel that satisfies the vessel occupancy rule is depicted by a vessel comparison ring.

14. The system as defined in claim 13, wherein the occupancy information is depicted on the display when a frozen image is depicted on the display by the ultrasound imaging system and when the size of the sample catheter has been selected.

15. The system as defined in claim 14, wherein the size of the sample catheter is configured to be selected by the user via the display.

16. The system as defined in claim 15, wherein the display is a touchscreen display.

17. The system as defined in claim 13, wherein the occupancy information includes a comparison between the selected sample catheter size and the minimum size of a sample vessel that satisfies the vessel occupancy rule.

18. The system as defined in claim 13, wherein the occupancy information includes a depiction of a cross-sectional portion of the imaged subcutaneous patient vessel, the depiction including the vessel comparison ring and a cross-sectional representation of the selected sample catheter disposed within the vessel comparison ring.

19. The system as defined in claim 13, wherein the vessel comparison ring is configured to be manually moved atop the imaged subcutaneous patient vessel by the user via touching and sliding on the display.

20. The system as defined in claim 18, further including an automatic vessel detection by the ultrasound imaging system configured to place the vessel comparison ring atop the imaged subcutaneous patient vessel.

21. The system as defined in claim 19, wherein the vessel comparison ring is configured to be manually re-sized by the user via touching and sliding a ring size control selector on the display.

22. The system as defined in claim 13, wherein the ultrasound imaging system is configured to enable the user to select one of a plurality of sample catheter sizes.

23. The system as defined in claim 13, wherein the rule user interface is configured to enable the selection of the vessel occupancy rule by one of at least a diameter and an area of the sample vessel, the rule user interface further including plus and minus selection icons to enable a user to adjust the vessel occupancy rule.

24. A method for using an ultrasound imaging system in preparation for inserting a catheter into a body of a patient, the method comprising:
selecting a vessel occupancy rule defining a maximum amount of occupation of a sample vessel by a sample catheter;
ultrasonically imaging a cross-sectional portion of a subcutaneous patient vessel of the patient by an ultrasound imaging device;
by a user interface, selecting a size of the sample catheter for insertion into the subcutaneous patient vessel; and
viewing occupancy information automatically generated by the ultrasound imaging device, the occupancy information including a comparison between the selected sample catheter size and a minimum size of a sample vessel that satisfies the vessel occupancy rule, wherein:
the minimum size of the sample vessel is depicted by a vessel comparison ring, and
the occupancy information includes a percentage amount of occupancy of the sample vessel by the selected sample catheter.

25. The method for using as defined in claim 24, wherein selecting the size of the sample catheter and viewing the occupancy information are performed using a display of the ultrasound imaging device.

26. The method for using as defined in claim 25, wherein the display includes a touchscreen display.

27. The method for using as defined in claim 26, wherein the vessel comparison ring is a dashed circle.

28. The method for using as defined in claim 27, wherein viewing the occupancy information includes viewing on the display a depiction of the cross-sectional portion of the imaged subcutaneous patient vessel, the depiction including the vessel comparison ring and a cross-sectional representation of the selected sample catheter disposed within the vessel comparison ring.

29. The method for using as defined in claim 24, further comprising moving the vessel comparison ring atop the imaged subcutaneous patient vessel manually via touching and sliding on the display.

30. The method for using as defined in claim 28, wherein viewing the occupancy information further includes employing an automatic vessel detection by the ultrasound imaging device to place the vessel comparison ring atop the imaged subcutaneous patient vessel.

31. The method for using as defined in claim 29, wherein viewing the occupancy information further includes altering a size of the vessel comparison ring via touching and sliding a ring size control selector on the display.

32. The method for using as defined in claim 31, further comprising selecting a new size of the sample catheter after viewing the occupancy information.

33. The method for using as defined in claim 24, wherein selecting the vessel occupancy rule further comprises selecting the vessel occupancy rule by one of at least a diameter and an area of the sample vessel, a display depicting a diameter selection icon including a vessel diameter depiction, the display further depicting an area selection icon including a vessel area depiction.

34. The method for using as defined in claim 24, wherein ultrasonically imaging the subcutaneous patient vessel further includes freezing the imaged subcutaneous patient vessel on a display, and wherein selecting the size of the sample catheter further includes providing a command to the ultrasound imaging system prior to selecting the size of the sample catheter.

35. The method for using as defined in claim 34, wherein providing the command includes pressing a control button on the display.

* * * * *